United States Patent [19]

Holtkamp

[11] Plant 4,782

[45] Oct. 27, 1981

[54] AFRICAN VIOLET PLANT

[76] Inventor: Reinhold Holtkamp, Werther Strasse 112, D-4294 Isselburg, Fed. Rep. of Germany

[21] Appl. No.: 165,076

[22] Filed: Jul. 1, 1980

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African Violet plant known by the cultivar name Glacier and particularly characterized by its large white, star-shaped flowers having five to eight petals; strong and upright flower stems; heart-shaped leaves, vigorous growth habit, and by its long lasting, non-dropping flowers.

1 Drawing Figure

The present invention comprises a new and distinct cultivar of African Violet plant, botanically known as *Saintpaulia ionantha,* and hereinafter referred to by the cultivar name Glacier.

Glacier is a product of a planned breeding program, and was identified during the breeding program resulting in the new cultivar by the breeding number E 163/1.

The new cultivar was originated from a cross made in a controlled breeding program in Isselburg, Rhineland, Germany. The female, or seed parent was identified as b. 287/9, and thereafter referred to by the cultivar name Alaska. Alaska is disclosed and claimed in U.S. Plant Pat. No. 4,557, issued June 24, 1980. Alaska is characterized by its large star-shaped white flowers having blue-violet centers and blue tinging at the edges. The male, or pollen parent was identified as NIT 86, an unpatented cultivar having star-shaped flowers white in color.

The new cultivar Glacier was discovered and selected as a flowering plant within the progeny of the stated cross by me in a controlled environment in Isselburg, Rhineland, Germany. Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Glacier, which in combination distinguish this African Violet as a new and distinct cultivar:

(1) Large white star-shaped flowers, partly to semi-double; five to eight petals, with the petal edges being waved;

(2) Strong, wire-like flower stems, upright with seven to twelve flowers;

(3) Heart-shaped flexible leaves, with serrated edges and velvety texture;

(4) Vigorous growth habit;

(5) Long lasting, non-dropping flowers;

(6) Very attractive and saleable plant with first flash of flowers.

The accompanying photographic drawing shows a typical specimen plant of the new cultivar. The colors appearing in the photograph are as true as possible with color illustrations of this type.

In the following description, color references are made to the Horticultural Color Chart issued by Wilson Colour Ltd., except where general color terms of ordinary significance are used, and where reference is made to the R.H.S. Color Chart for petal color.

Botanical classification: *Saintpaulia ionantha,* Ramat. cv Glacier.

Parentage:

*Male parent.*—NIT 86.

*Female parent.*—b. 287/9 (Alaska).

Propagation: The new cultivar holds its distinguishing characteristics through successive propagations by leaf cuttings and by division of shoots.

Plant: From 10 cm. to 12 cm. tall when grown in pots, and approximately 30–40 cm. in diameter when fully grown.

*Leaves.*—General form: heart-shaped. Diameter: 90 mm. in width and up to 110 mm. in length. Texture: soft, velvety, slightly hairy. Aspect: slightly shiny. Veins: visible from above, well pronounced from below; shiny. Color (upperside): HCC 00962, parsley green. Color (underside): HCC 00862/3, willow green. Petiole: light green, hairy; HCC spinach green, lighter than 0960/3.

Flowers:

*Buds.*—Ball-shaped; before opening 8–10 mm. in diameter, color pod green, HCC 061/1.

*Sepals.*—5 or 6, light green, hairy. Color: HCC 061/1; spear-shaped, hairy.

*Calyx.*—Flat funnel-shaped.

*Aspect.*—Flower stem and receptacle connected.

*Peduncles.*—Hairy, erect.

Individual flowers:

*Size.*—Up to 45–55 mm. in diameter.

*Color.*—Upperside (mature): snow white, crystal-like, R.H.S. 155D. Underside (mature): snow white, shiny. Immature flowers when just opening are light greenish white.

*Borne.*—Flower stems have 7–12 flowers on strong peduncles.

*Shape.*—Flowers normally have 5–6 large petals; occasionally, flowers will display a small petal in the center.

*Corolla.*—Strong upright peduncles with up to 12 flowers; edges of petals are slightly waved.

*Flowering time.*—In 7–9 weeks after potting, a saleable plant with decorative flower head is produced.

*Reproductive organs.*—Stamens: 10–12 compact cells. Anthers: 10–12, close together, color HCC Dresden yellow 64/2-64/3. Filaments: 3–4 mm. long; flat to round. Styles: 7–9 mm. long, white. Pollen color: HCC 64/1.

*Roots.*—Young root tips are white, turning brownish quite rapidly; root system generally strong and well established.

*Disease resistance.*—No disease problems noted to date.

General observations: Glacier is a vigorous growing variety with large glittery star-shaped flowers, ideal for larger pots, 5–6 inches in diameter. The new cultivar has upright and strong flower stems carrying 7–12 flowers, which are long lasting and non-dropping.

I claim:

1. A new and distinctive cultivar of African Violet plant known by the cultivar name Glacier, as described and illustrated, and particularly characterized by its large white, star-shaped flowers having five to eight petals; strong and upright flower stems; heart-shaped leaves, vigorous growth habit, and by its long lasting, non-dropping flowers.

* * * * *

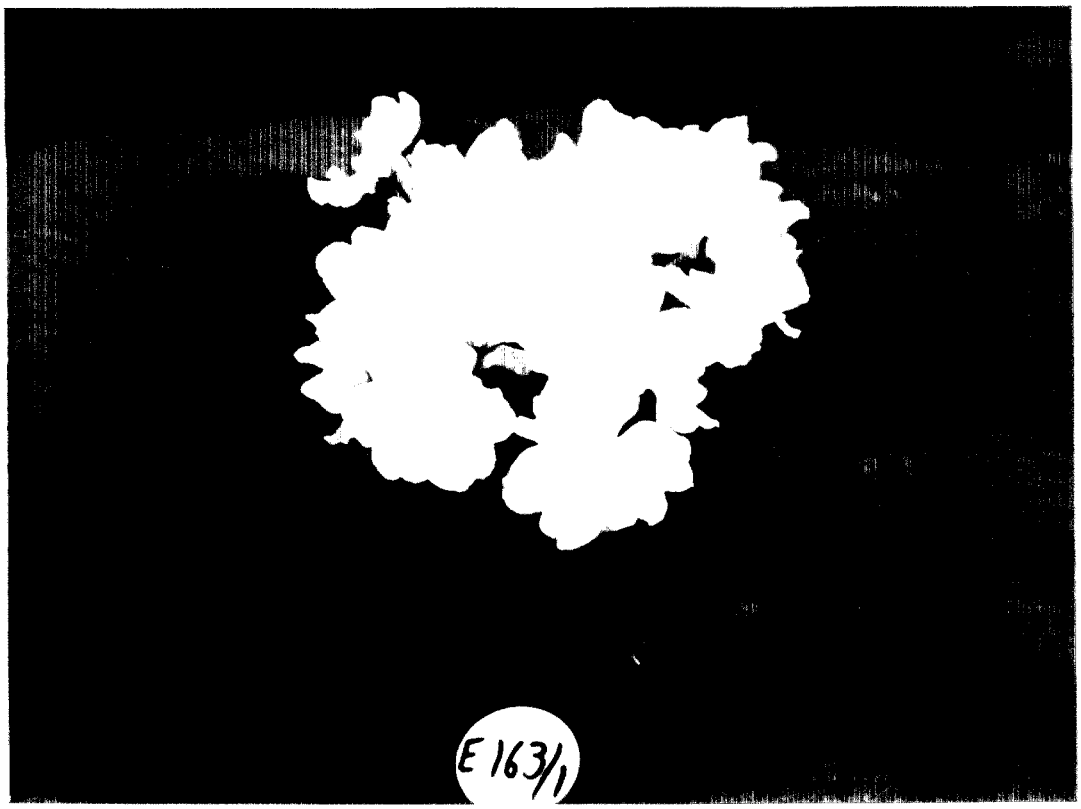
E 163/1